United States Patent
Miyamoto et al.

(10) Patent No.: US 8,889,652 B2
(45) Date of Patent: Nov. 18, 2014

(54) PHARMACEUTICAL AGENT HAVING LONG-LASTING EFFECT OF TREATING ARTHRITIC DISORDERS

(75) Inventors: Kenji Miyamoto, Higashiyamato (JP); Keiji Yoshioka, Higashiyamato (JP); Katsuya Takahashi, Higashiyamato (JP)

(73) Assignee: Seikagaku Corporation, Tokyo (JP)

( * ) Notice: Subject to any disclaimer, the term of this patent is extended or adjusted under 35 U.S.C. 154(b) by 346 days.

(21) Appl. No.: 12/448,064

(22) PCT Filed: Dec. 6, 2007

(86) PCT No.: PCT/JP2007/073987
§ 371 (c)(1),
(2), (4) Date: Jun. 29, 2009

(87) PCT Pub. No.: WO2008/069348
PCT Pub. Date: Jun. 12, 2008

(65) Prior Publication Data
US 2011/0053885 A1 Mar. 3, 2011

Related U.S. Application Data

(60) Provisional application No. 60/868,798, filed on Dec. 6, 2006.

(51) Int. Cl.
*A61K 31/728* (2006.01)
*A61K 31/738* (2006.01)
*A61P 19/02* (2006.01)

(52) U.S. Cl.
CPC ............. *A61K 31/728* (2013.01); *A61K 31/738* (2013.01)
USPC .......................................................... 514/54

(58) Field of Classification Search
None
See application file for complete search history.

(56) References Cited

U.S. PATENT DOCUMENTS

| | | | |
|---|---|---|---|
| 5,356,883 A | 10/1994 | Kuo et al. | |
| 5,462,976 A | 10/1995 | Matsuda et al. | |
| 5,763,504 A | 6/1998 | Matsuda et al. | |
| 6,031,017 A | 2/2000 | Waki et al. | |
| 6,107,410 A | 8/2000 | Waki et al. | |
| 6,602,859 B2 | 8/2003 | Miyamoto et al. | |
| 7,014,860 B1 | 3/2006 | Kawata et al. | |
| 7,931,030 B2 | 4/2011 | Bailleul | |
| 2002/0143121 A1 | 10/2002 | Miyamoto et al. | |
| 2006/0148755 A1 | 7/2006 | Bailleul | |
| 2009/0118348 A1 | 5/2009 | Miyamoto et al. | |
| 2012/0142629 A1 | 6/2012 | Hosokawa et al. | |

FOREIGN PATENT DOCUMENTS

| | | |
|---|---|---|
| EP | 0 718 312 A2 | 6/1996 |
| EP | 0 939 086 A1 | 9/1999 |
| JP | 5-74571 B2 | 10/1993 |
| JP | 2002-348243 A | 12/2002 |
| JP | 2003-252905 A | 9/2003 |
| WO | WO 2007/004675 A1 | 1/2007 |

OTHER PUBLICATIONS

Barbucci, R. et al "Hyaluronic acid hydrogel in the treatmetn of osteoarthritis" Biomaterials (2002) vol. 23, pp. 4503-4513.*
Miyamoto et. al. "Evaluation of in vivo biocompatibility and biodegradation of photocrosslinked hyaluronate hydrogels (HADgels)", J. Biomed Mater Res. A 70:550-559(2004).
Seikagaku Corporation, "Start of a Clinical Trial in the United States of Cross-Linked Hyaluronate Hydrogel", Securities code: 4548, Jul. 18, 2006, 3 pages.
Extended European Search Report issued in European Patent Application EP 11167846.2 on Oct. 17, 2011.
Office Action issued in Australian Patent Application No. 2007328871on May 18, 2012.
Office Action issued in Chinese Patent Application No. 200780045074.5 on Jul. 26, 2012.
Office Action issued in European Patent Application No. EP 11 167 846.2 on Oct. 22, 2012.
Office Action issued in Japanese Patent Application No. 2009-524032 on Feb. 12, 2013.
Office Action issued in Taiwanese Patent Application No. 096146443 on Nov. 20, 2012.
Altman et al., "Efficacy and saftey of a single intra-articular injection of non-animal stabilized hyaluronic acid (NASHA) in patients with osteoarthritis of the knee", Osteoarthritis and Cartilage, (2004), vol. 12, pp. 642-649.
Office Action issued on Dec. 13, 2010 in counterpart Chinese Application No. 200780045074.5 and its English Translation.
Office Action issued on Feb. 17, 2012 in the counterpart Chinese Application No. 200780045074.5 and its English Translation.
Office Action issued Sep. 17, 2009 for counterpart European Application No. 078750518.7.
Summons to Attend Oral Proceedings issued on Dec. 22, 2010 in counterpart European Application No. 07850518.7.
Raman, R. et al., "Efficacy of Hylan G-F 20 and sodium hyaluronate . . .", The Knee (2008), vol. 15, pp. 318-324.
Office Action dated Nov. 8, 2013 in U.S. Appl. No. 13/390,261, published as US 2012/0142629 A1.
Australian Office Action in regards to Australian Application No. 2007328871, dated Sep. 25, 2013.
Canadian Office Action in regards to Canadian Application No. 2,672,002, dated Nov. 29, 2013.
European Office Action in regards to European Application No. 11167846.2, dated Sep. 27, 2013.
Summons to attend oral hearing in regards to European Application No. 11167846.2, dated Mar. 28, 2014.

* cited by examiner

*Primary Examiner* — Leigh Maier
(74) *Attorney, Agent, or Firm* — Greenblum & Bernstein, P.L.C.

(57) ABSTRACT

The present invention relates to an injection solution for intra-articular administration for treating arthritic disorders comprising a cross-linked hyaluronic acid derivative wherein part of functional groups of a hyaluronic acid are cross-linked with a cross-linking group to the extent of 0.6 to 15% of cross-linking extent as an active ingredient in an amount having a long-lasting analgesic effect and a pharmaceutically acceptable carrier, and an analgesic composition for suppressing a cartilage degeneration caused by arthritic disorders or a composition for suppressing a cartilage degeneration or an inflammation of synovium caused by arthritic disorders each comprising the cross-linked hyaluronic acid derivative and a pharmaceutically acceptable carrier.

21 Claims, 10 Drawing Sheets

PHARMACEUTICAL AGENT HAVING LONG-LASTING EFFECT OF TREATING ARTHRITIC DISORDERS

This application is the National Phase of PCT/JP2007/073987 filed on Dec. 6, 2007, which claims priority under 35 U.S.C. 119(e) to U.S. Provisional Application No. 60/868,798 filed on Dec. 6, 2006, all of which are hereby expressly incorporated by reference into the present application.

FIELD OF THE INVENTION

This invention relates to pharmaceutical products having a long-lasting analgesic effect, a cartilage protective effect, and an anti-inflammatory effect for a long term by a single injection.

BACKGROUND ART

Osteoarthritis (OA), the clinical syndrome of joint pain and dysfunction caused by joint degeneration, affects more people than any other joint disease. Osteoarthritis is by far the most common joint disorder in the United States and throughout the world, and is one of the leading causes of disability in the elderly. Knee OA is a common but often difficult problem to manage in primary care. Traditional nonsurgical management, consisting of lifestyle modification, physical therapy and pharmacologic therapy, is often ineffective or leaves residual symptoms. An option for subjects with symptomatic knee OA is a treatment that involves a series of intra-articular injections of hyaluronic acid (hereinafter referred to IA-HA). Sodium hyaluronate is a naturally-occurring constituent of extra cellular matrix, and following intra-articular injection works as a lubricant and shock absorber to relieve pain and improve knee function in OA. Currently, there are 5 IA-HA commercially available products in the United States, SUPARTZ®, SYNVISC®, HYALGAN®, ORTHOVISC® and EUFLEXXA. SYNVISC® was the first IA-HA product launched in the US, and the only aqueous solution of cross-linked derivatives of hyaluronate, others are aqueous solutions of sodium hyaluronate (hereinafter referred to HA-Na). These currently marketed IA-HA products are not apparent differenced in effectiveness. Moreover these products utilize a series of 3 to 5 injections and in other words do not result in longer term responses by a single injection. Therefore new IA-HA product requiring fewer injections would be expected to reduce invasiveness and potential risk of joint infection and result in longer term responses by a single injection.

So far there are many reports about cross-linked hyaluronate with the different cross-linking methods from SYNVISC®, for example cross-linked hyaluronate produced by using multifunctional epoxy compound as a cross-linking group (see Patent Literature 1), photo cross-linked hyaluronate (see Patent Literatures 2 to 4) and intramolecular bridged hyaluronate without a cross linker (see Patent Literature 5). Cross-linked hyaluronate is being investigated as a minimally invasive treatment for pain associated with osteoarthritis of the knee in subjects who have failed to respond adequately to conservative non-pharmacologic therapy and/or simple analgesics, e.g., acetaminophen. For example, it is reported an injected agent for treating joint disorder which was improved to produce a merit of decreasing number of doses by using an agent comprising hyaluronate gel with or without cross-linked structure and phospholipids (see Patent Literature 6).

However, many reports about photo cross-linked hyaluronate product are mainly noted synthesis and general properties of the product and does not carefully examined available and restrictive conditions and properties for an unique application and a specific effect on said cross-linked hyaluronate product. The comparison of antigenicity and irritant property between SYNVISC® and photo cross-linked hyaluronate was reported on Reference (see Non-Patent Literature 1).

Patent Literature 1: JP-B2-5-74571
Patent Literature 2: U.S. Pat. No. 5,462,976
Patent Literature 3: U.S. Pat. No. 5,763,504
Patent Literature 4: U.S. Pat. No. 6,031,017
Patent Literature 5: JP-A-2003-252905
Patent Literature 6: JP-A-2002-348243
Non-Patent Literature 1: "Evaluation of in vivo biocompatibility and biodegradation of photocrosslinked hyaluronate hydrogels" J. Biomed Mater Res. A 70:550-559 (2004)

SUMMARY OF THE INVENTION

Disclosure of the Invention

This invention was developed to solve the problem of the previously available IA-HA product that the effect of the products does not last or continue over several weeks.

That is, the present invention is as follows:

[1] An injection solution for intra-articular administration for treating arthritic disorders comprising a cross-linked hyaluronic acid derivative wherein part of functional groups of a hyaluronic acid are cross-linked with a cross-linking group to an extent of 0.6% to 15% of cross-linking extent based on a total number of constituent disaccharide unit of hyaluronic acid as an active ingredient in such an amount that shows a long-lasting analgesic effect or a long-continued analgesic effect, and a pharmaceutically acceptable carrier.

[2] The injection solution as described in [1], wherein a degree of substitution of the cross-linking group of the cross-linked hyaluronic acid derivative is 3% to 50% based on a total number of constituent disaccharide unit of the cross-linked hyaluronic acid derivative.

[3] The injection solution as described in [1], wherein a degree of cross-linking of the cross-linked hyaluronic acid derivative is 5% to 40% based on a total number of constituent cross-linking group.

[4] An injection solution for intra-articular administration for treating arthritic disorders comprising a cross-linked hyaluronic acid derivative wherein a degree of substitution of a cross-linking group of the cross-linked hyaluronic acid derivative is 3% to 50% based on a total number of constituent disaccharide unit of hyaluronic acid and a degree of cross-linking is 5% to 40% based on a total number of constituent cross-linking group, and a pharmaceutically acceptable carrier.

[5] An injection solution for intra-articular administration for treating arthritic disorders comprising a cross-linked hyaluronic acid derivative wherein a degree of substitution of a cross-linking group is 3% to 50% based on total number of constituent disaccharide unit of hyaluronic acid, a degree of cross-linking is 5% to 40% based on a total number of constituent cross-linking group, and a cross-linking extent is 0.6% to 15% based on a total number of constituent disaccharide unit of hyaluronic acid, and a pharmaceutically acceptable carrier.

[6] The injection solution as described in any one of [1] to [5], wherein a concentration of a solution of said cross-linked hyaluronic acid derivative is 0.5% by weight to 3.0% by weight based on the total weight of the solution.

[7] The injection solution as described in any one of [1] to [6], wherein a residual ratio in synovial fluid of the cross-linked hyaluronic acid derivative on 3 days after intra-articular administration of the solution is not less than 15% compared with the cross-linked hyaluronic acid derivative administered when the concentration of the solution of the cross-linked hyaluronic acid derivative is about 1% by weight.

[8] The injection solution as described in any one of [1] to [6], wherein said analgesic effect lasts or continues for 2 weeks or more after administration of the solution at the site of administration.

[9] The injection solution as described in [1], comprising the cross-linked hyaluronic acid derivative in the form of unit dosage, wherein the unit dosage comprises 0.3 mg to 1.2 mg per kg of the cross-linked hyaluronic acid derivative on one administration.

[10] The injection solution as described in [1], wherein the cross-linked hyaluronic acid derivative has the following characteristics;
a weight average molecular weight of hyaluronic acid is from 500,000 to 2,500,000,
a cross-linking group is a residue of cinnamic acid or cinnamic acid derivatives,
a spacer is a residue of aminoalkyl alcohol,
a degree of substitution of a cross-linking group is from 10% to 25%, and
a degree of cross-linking in the cross-linked hyaluronic acid derivative is from 10% to 30%, and wherein a concentration of the solution of the cross-linked hyaluronic acid derivative is from 0.7% by weight to 2.0% by weight.

[11] A pharmaceutical composition for intra-articular administration for treating arthritic disorder comprising a cross-linked hyaluronic acid derivative wherein part of carboxyl groups of hyaluronic acid are cross-linked each other with cross-linking group to form crosslinks via amide bonds and a pharmaceutically acceptable carrier, and having a sustainable analgesic effect.

[12] The composition as described in [11], wherein a hyaluronic acid is cross-linked to form the cross-linked hyaluronic acid derivative by a photodimerization reaction or by a photopolymerization reaction with irradiation of light of cross-linking groups having amino group and wherein a carboxyl group of the hyaluronic acid is bound to the amino group of the cross-linking group.

[13] The composition as described in [11] or [12], wherein the carboxyl groups of the hyaluronic acid are cross-linked with the cross-linking group to an extent of 0.6% to 15% of cross-linking extent based on a total number of constituent disaccharide unit of hyaluronic acid.

[14] The composition as described in any one of [11] to [13], wherein said analgesic effect lasts or continues for 2 weeks or more after administration of the composition at the site of administration.

[15] The composition as described in any one of [11] to [14], wherein a residual ratio in synovial fluid of the cross-linked hyaluronic acid derivative on 3 days after intra-articular administration of the composition is not less than 15% compared with the cross-linked hyaluronic acid derivative administered when a concentration of a solution of the cross-linked hyaluronic acid derivative is about 1% by weight.

[16] An analgesic composition for alleviating joint pain caused by arthritic disorders comprising a cross-linked hyaluronic acid derivative wherein part of functional groups of a hyaluronic acid are cross-linked with a cross-linking group to an extent of 0.6% to 15% of cross-linking extent based on a total number of constituent disaccharide unit of hyaluronic acid as an active ingredient in such an amount that shows a long-lasting analgesic effect or a long-continued analgesic effect, and a pharmaceutically acceptable carrier.

[17] A composition for suppressing a cartilage degeneration caused by arthritic disorders comprising a cross-linked hyaluronic acid derivative wherein part of functional groups of a hyaluronic acid are cross-linked with a cross-linking group to an extent of 0.6% to 15% of cross-linking extent based on a total number of constituent disaccharide unit of hyaluronic acid as an active ingredient in such an amount that shows a long-lasting suppressing effect or a long continued suppressing effect, and a pharmaceutically acceptable carrier.

[18] A composition for suppressing a inflammation of synovium caused by arthritic disorders comprising a cross-linked hyaluronic acid derivative wherein part of functional groups of a hyaluronic acid are cross-linked with a cross-linking group to an extent of 0.6% to 15% of cross-linking extent based on a total number of constituent disaccharide unit of hyaluronic acid as an active ingredient in such an amount that shows a long-lasting suppressing effect or a long continued suppressing effect, and a pharmaceutically acceptable carrier.

[19] The composition as described in any one of [16] to [18], wherein said arthritic disorder is osteoarthritis.

[20] The composition as described in [19], wherein said arthritic disorder is traumatic arthritic disorder.

[21] A kit comprising a syringe filled with an injection solution or a composition as described in any one of [1] to [20].

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 2A is a typical specimen from the phosphate buffer saline (PBS) group.

FIG. 2B is a typical specimen from 1% sodium hyaluronate solution (1% HA-Na) group.

FIG. 2C is a typical specimen from 1 injection Cross-linked hyaluronate gel (HA-Gel) group.

FIG. 2D is a typical specimen from 2 injections HA-Gel group.

FIG. 3A is a graph showing analgesic effects of HA-Gel administered intra-articularly 1 week before bradykinin injection.

FIG. 3B is a graph showing analgesic effects of HA-Gel administered intra-articularly 2 week before bradykinin injection.

FIG. 3C is a graph showing analgesic effects of HA-Gel administered intra-articularly 4 week before bradykinin injection.

DESCRIPTION OF THE PREFERRED EMBODIMENTS

Figure 1:
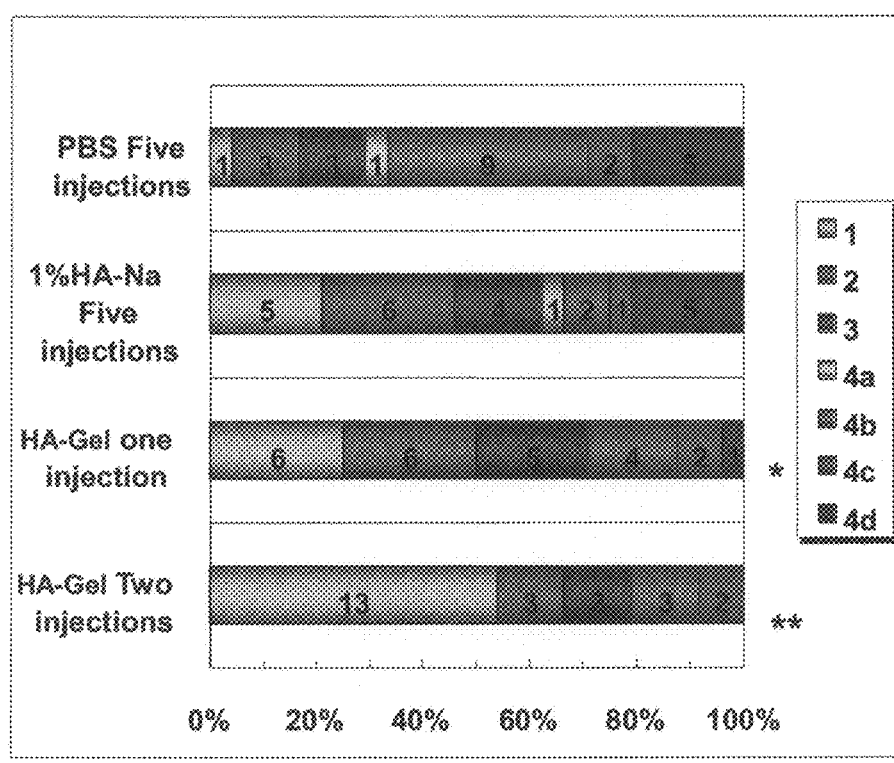
FIG. 1 is a graph showing rabbit Anterior Cruciate Ligament (ACL) transection study: gross morphological assessment wherein number of animals=12 per group; *$P<0.05$, **$P<0.01$ vs. PBS.

Hereinafter, the present invention is described below in details by way of detailed embodiments and methods. These detailed description are intended only to be examples of the inventions disclosed and claimed herein and are in no way intended to limit the scope of the invention which is particularly pointed out and distinctly claimed in the numbered claims appended hereto.

In this specification, the "osteoarthritis", "hyaluronic acid" and "sodium hyaluronate" are referred to as "OA", "HA" and "HA-Na", respectively, and a compound which may be used as a spacer is referred to as "a spacer compound".

A cross-linked-hyaluronic acid derivative or a cross-linked hyaluronic acid compound to be used in the present invention (hereinafter referred to a cross-linked HA derivative) has a cross-linked structure formed by intra-molecular cross-linking or inter-molecular cross-linking via cross-linking groups which are bonded covalently to HA. The cross-linked structure makes the cross-linked HA derivative a three-dimensional networking structure, thereby a solution dissolving the cross-linked HA derivative to an aqueous medium has a physical property of viscoelastic hydrogel. The solution has higher viscosity than a HA solution in the same concentration condition.

The cross-linked HA derivative may be either in a free form of not forming a salt or a pharmaceutically acceptable salt. For example the pharmaceutically acceptable salt of a cross-linked HA derivative includes a sodium salt, a potassium salt, a magnesium salt, a calcium salt and the like.

A hyaluronic acid to be used in the present invention is not particularly limited in so far as it's a glycosaminoglycan which consists of a disaccharide unit consisting of N-acetyl-D-glucosamine and D-glucuronic acid bound through a β1,3 bond as the basic core structure and is constructed by repeating a β1,4 bond of the disaccharide unit, namely a generally used hyaluronic acid (HA).

The HA to be used may be either in a free form of not forming a salt or a pharmaceutically acceptable salt. The pharmaceutically acceptable salt of HA includes salts with alkali metal ions such as a sodium salt, a potassium salt, salts with alkaline earth metal ions such as a magnesium salt, and a calcium salt, salt with inorganic base such as ammonium salt, and salt with organic base such as diethanolamine, cyclohexylamine and amino acid. The HA salt is preferably a salt with alkali metal ion, particularly a salt with a sodium ion, because of its high affinity for the living body.

The HA to be used may be derived from natural products by extracting from partial materials of living organisms (such as cockscomb, umbilical cord, cartilage, skin, etc). And it also may be chemically synthesized or may be produced in microorganisms such as yeast by genetic engineering. Especially it is preferably used HA which has high purity and does not substantially include unacceptable impurities on drug.

The weight average molecular weight of HA is not particularly limited, but from 10,000 to 5,000,000 can be exemplified. Preferably from 200,000 to 3,000,000, and more preferably from 500,000 to 2,500,000 can be exemplified.

A cross-linking form to be used in the present invention is preferably a cross-linking form making use of a covalent bond because of good binding stability.

A cross-linking group to be used in the present invention is preferably exemplified a photoreactive cross-linking group (i.e., cross-linking group having a photoreactive residue) which may be selected any residue of compounds capable of undergoing a photodimerization reaction or a photopolymerization reaction by irradiation with light (ultraviolet rays). For example, as said residues of the compounds, there are residues of cinnamic acid, substituted cinnamic acids, acrylic acid, maleic acid, fumaric acid, sorbic acid, coumarin, thymine or the like. Among these compounds, preferred are those compounds having a vinylene group capable of forming a cyclobutane ring by light irradiation, and cinnamic acid or substituted cinnamic acids are more preferred from the point of view of photoreactivity and safety for a living body.

The substituted cinnamic acids may be exemplified by cinnamic acid derivatives and the like in which one or two hydrogen atoms at any positions of the benzene ring of cinnamic acid are substituted by a lower alkyl group having 1 to 8 carbon atoms (e.g., methyl, ethyl, propyl, isopropyl, butyl, tert-butyl and the like), a lower alkoxyl group having 1 to 8 carbon atoms (e.g., methoxy, ethoxy, propoxy, isopropoxy, butoxy and the like), an amino group, a hydroxyl group and the like, and preferably exemplified by aminocinnamic acid and p-aminocinnamic acid.

The cross-linked HA derivative to be used in the present invention is necessary to have appropriate resistance to body's internal metabolic environment, such as pH, ionic strength, temperature and the like, which helps long-lasting or long-continued effects at the administration site. It is preferred to be an amide bond, whereby the residue of compound to be a cross-linking group is introduced into a carboxyl group of HA, because amide bond has a better resistance to hydrolysis under acidic or alkaline conditions.

The photoreactive cross-linking group above-mentioned may also be introduced into a carboxyl group of HA via a residue of compounds having an amino group which is called a spacer. In addition, using a spacer provides improvement of a reaction with the cross-linking group and HA and a photo cross-linking reaction.

A compound to be used as a spacer in the present invention is not particularly limited in so far as it is a compound having at least one amino group and a functional group capable of binding to a photoreactive cross-linking group, for example, aminoalkyl alcohols, diamines, amino acids, peptides and the like can be cited preferably. Considering a desirable resistant to metabolic degradation and an appropriate conservation of properties on the cross-linked HA derivative during an intra-articular administration, it is preferably exemplified by aminoalkyl alcohols having from 2 to 18 carbon atoms, and more preferably aminoalkyl alcohols having 2 to 12 carbon atoms. Especially preferably aminopentanol, aminobutanol, aminopropanol and aminoethanol can be exemplified because of giving a suitable distance between HA and a photoreactive cross-linking group on a cross-linking reaction.

Unless otherwise noted, in this specification, the cross-linking group may include a cross-linking group which is introduced into a residue of a spacer compound, accordingly a photoreactive cross-linking group may also include a photoreactive cross-linking group which is introduced into a residue of a spacer compound. And a cross-linking group which forms a cross-linked structure is occasionally referred to as a cross-linked group and a cross-linking group which is not cross-linked is sometimes referred to as a cross-linkable group.

A method for synthesizing the cross-linked HA derivative of the present invention is not particularly limited, in so far as it is a method for being possible to bind chemically HA to a compound which can be a cross-linking group via amide bond, for example, a method using a water-soluble condensing agent such as a water-soluble carbodiimide, e.g., 1-ethyl-3-(3-dimethylaminopropyl) carbodiimide hydrochloride (EDCI.HCl), 1-cyclohexyl-3-(2-morpholinoethyl) carbodiimide-metho-p-toluenesulfonate, 1-cyclohexyl-3-(2-morpholinoethyl)carbodiimide hydrochloride and the like; a method using an auxiliary condensing agent such as N-hydroxy succinimide (HOSu) and N-hydroxy benzotriazole (HOBt) in addition to the above condensing agent; a method using a condensing agent such as 4-(4,6-dimethoxy-1,3,5-triazin-2-yl)-4-methylmorpholinium chloride (DMT-MM) and the like; active esterification method; acid anhydride method and the like. In addition, when a cross-linking group into which a spacer is introduced is used as a cross-linking group, it may be either a method in which a spacer compound is introduced into HA in advance and then a cross-linking group is introduced into the spacer-linked HA or a method in which a spacer is introduced into a cross-linking group in advance, and then the spacer-linked cross-linking group is introduced into HA.

Hereinafter, for simplify a representation, a cross-linking group-linked HA derivative produced by the above described method without building a cross-linked structure yet is occasionally referred to as a non-cross-linked product or a non-cross-linked compound.

A method for crosslinking a non-cross-linked product is not particularly limited, in so far as a method to may produce to form a cross-linked structure by reacting between cross-linking groups.

For example, in case of the non-cross-linked product using a photo cross-linking group, it is preferred to a method by irradiating a solution dissolving the non-cross-linked product homogeneously with light.

Although HA in itself has good solubility in an aqueous medium, in case of hyaluronic acid derivative in which a spacer compound is introduced into to the carboxyl group owned by hyaluronic acid which contribute to it's hydrophilic property, the hydrophilic property decreases as the degree of substitution increases.

Therefore, the above described method for synthesizing the non-cross-linked product preferably includes a method which comprises carrying out an alkali treatment for improving a solubility in an aqueous medium of the non-cross-linked product.

A method of alkali treatment is not particularly limited, in so far as it is a treatment by which a solution becomes alkaline. An alkali agent used may be in the form of either organic or inorganic salts. In consideration of treatment in the aqueous solvent, the use of the inorganic alkali salts is preferred. Among these inorganic alkali salts, weak alkali salts such as sodium hydrogen carbonate and sodium carbonate are more suitably used as compared to strong alkali salts such as sodium hydroxide since such weak alkali salts have a less influence on conversion of cross-linking group-linked hyaluronic acid derivative into low-molecular compounds or decomposition of the cross-linking group. Here, the alkali treatment may be conducted at a pH value of usually 7.2 to 11, preferably 7.5 to 10. The amount of the alkali used and the alkali-treating time may be appropriately controlled depending upon the aimed hydrophilic property. For example, when sodium hydrogen carbonate is used in an amount of 500 mg based on 1 g of hyaluronic acid (i.e., in a molar amount 10 times or more the mole of hyaluronic acid), the alkali treatment may be conducted for 2 to 3 hours under stirring, thereby obtaining the non-cross-linked compound having a sufficiently enhanced hydrophilic property. A 1.0% by weight solution of the non-cross-linked derivative obtained by the above method is capable of passing through a porous filter having a pore size of 0.45 vim and a diameter of 25 mm at a rate of not less than 2 mL/minute at 24° C. under a pressure of 5.0 $Kg/cm^2$.

It is preferred that light irradiation (photoirradiation) of a non-cross-linked product is carried out under such conditions that the photoreactive cross-linking group efficiently causes a photodimerization or a photopolymerization reaction.

A kind and wavelength of light to be used is not particularly limited, in so far as a light which may be selected from those having a wavelength capable of subjecting the photoreactive cross-linking group to a photoreaction without cleavage of glycoside bond of the hyaluronic acid. For example, when a cross-linking group to be used is a cinnamic acid or a cinnamic acid derivative, an ultraviolet light having a wavelength of 200 to 600 nm is preferred. An integration of the irradiated light is appropriately selected depending on a desired property of the resultant, a desired degree of substitution, a concentration of the non-cross-linked product solution and the like. As a preferred light source, there may be used an ultraviolet lamp, a high-pressure mercury lamp or a metal halide lamp. Preferably, if necessary, undesired wavelengths may be removed from the light source, for example, by a cut filter.

The cross-linked HA derivative of the present invention has a cross-linked structure formed by intra-molecular cross-linking or inter-molecular cross-linking via cross-linking groups which are bonded covalently to HA. The cross-linked structure makes the cross-linked HA derivative a three-dimensional networking structure, thereby a solution of the cross-linked HA derivative has a physical property of viscoelastic hydrogel composed of viscous and elastic. The physical property is affected by contributing factors such as a degree of substitution of a cross-linking group, a degree of cross-linking, a concentration of a cross-linkable compound on cross-linking reaction and the like. And therefore it is important to set up these factors at an appropriate range.

These suitable ranges may be decided appropriately depending on a desired property of a resultant. For example, a degree of substitution of a cross-linking group of the present invention is preferably 3% to 50%, more preferably 5% to 30% and much more preferably 10% to 25% based on a total number of constituent disaccharide unit of HA. A preferred concentration of a reaction solution on cross-linking reaction may be exemplified 0.5% to 10%, more preferably 0.7% to 2% based on a total weight of the solution. A degree of cross-linking is exemplified preferably 5% to 40%, more preferably 7% to 35% and much more preferably 10% to 30% based on a total number of constituent cross-linking group.

In addition, the degree of substitution (DS) can be calculated on the ratio (%) of introduction of a cross-linking group per constituent disaccharide unit of HA, for example, DS on the non-cross-linked compound having one cross-linking group per constituent disaccharide unit or one cross-linking group per constituent 200 saccharide units is 100% or 1%, respectively.

The degree of cross-linking can be calculated on the ratio (%) of cross-linked groups to the introduced cross-linking groups. For example, in the case of the HA derivatives having 100 cross-linking groups if 20 cross-linking groups (monomers) react into 10 dimmers, the degree of cross-linking is 20%.

It is commonly agreed that it is difficult to get a hydro-gel solution having moderate fluidity if a cross-linked hyaluronic acid derivative to be a solute are excessive amount with compared to medium (solvent) and there are excessive bridge formation in a cross-linked hyaluronic acid derivative.

The cross-linked HA derivative of the present invention needs a property of moderate fluidity for intra-articular administration by a needle-tipped syringe. Meanwhile it needs also an appropriate resistance to body's internal metabolic environment and a suitable retention capability at administration site. Therefore, it is not preferred to be much low DS or degree of cross-linking. Consequently, a balance of viscosity and elasticity is important.

The solution of a cross-linked HA derivative designed according to the above mentioned conditions can be an injectable solution capable passing through a needle having from 18 gauge to 25 gauge and can be used an injection solution for intra-articular administration.

For example, from the standpoint of a cross-linking extent which is a product of DS and a degree of cross-linking and is expressed as in terms of molar ratio (%) of dimmers of cross-linking group per constituent disaccharide unit of HA, the cross-linked HA derivative of the present invention is preferred to have a cross-linking extent in the range from 0.6% to 15%, more preferably in the range from 1.0% to 7.5% based on a total number of constituent disaccharide unit of HA.

As shown in the examples which are described below, the cross-linked HA derivative of the present invention showed a more significant analgesic effect by a single injection, not by a series of 3 to 5 injections for one treatment period. And it also showed keeping an analgesic effect for a long term than a solution of HA alone, and showed an effective and long-lasting or long-continued analgesic effect on both acute pain and chronic pain. Moreover, it also provides an anti-inflammatory effect on synovium and a cartilage protective effect for a long term by a single time injection.

According to the present invention, it is possible to provide an injection solution and a pharmaceutical composition for intra-articular administration for treating arthritic disorders including OA, traumatic arthritis, inflammatory arthritic disorder, degenerative arthritic disorder and the like. The injection solution comprises the cross-linked hyaluronic acid derivative of the present invention as an active ingredient and a pharmaceutically acceptable carrier, and similarly the pharmaceutical composition comprises the cross-linked hyaluronic acid derivative of the present invention as an active ingredient and a pharmaceutically acceptable carrier.

The pharmaceutically acceptable carrier is exemplified an aqueous medium as which is used for a solution of the cross-linked HA derivative of the present invention. For example there are water for injection, physiological saline, and phosphate buffered saline. Also it may be acceptable an additive to be usually used for the injection such as an pH adjuster and tonicity agent unless the injection solution and the pharmaceutical composition of the present invention lose a desired therapeutic effect and produce side-effects. For example there are sodium dihydrogen phosphate, disodium hydrogen phosphate, and sodium chloride.

The injection solution and the pharmaceutical composition are effective fully by a fewer number of doses for a duration of therapy than the number of doses of commercially available IA-HA products (i.e., a series of 3 to 5 times injections for a duration of therapy).

And also it is possible to provide a kit comprising a syringe filled with a solution of the cross-linked HA derivative of the present invention, if necessary, which may be equipped with a plunger, a plunger rod and the like.

A cross-linked HA derivative produced according to the above mentioned method and conditions can be used for the injection solution and the pharmaceutical composition. Preferable cross-linked HA used for the injection solution or the pharmaceutical composition has the following parameters as for cross-link;

a cross-linking extent of from 0.6% to 15% and a degree of substitution of from 3% to 50%, a cross-linking extent of from 0.6% to 15% and a degree of cross-linking of from 5% to 40%, a degree of substitution of from 3% to 50% and a degree of cross-linking of from 5% to 40%, a cross-linking extent of from 0.6% to 15%, a degree of substitution of from 3% to 50%, and a degree of cross-linking of from 5% to 40%, or a cross-linking extent of from 1% to 7.5%, a degree of substitution of from 10% to 25%, and a degree of cross-linking of from 10% to 30%.

A disease to be treated by the pharmaceutical agent of the present invention is not particularly limited, and it is possible to be used as a therapeutic agent for alleviating joint pain caused by arthritic disorders and suppressing an inflammation of synovium caused by arthritic disorders, suppressing a cartilage degeneration caused by arthritic disorders and improving a range of motion on joint. In addition, it is possible to use the same not only for treatment but also for prevention of the above-mentioned diseases.

A dose of the injection solution or the pharmaceutical composition is not particularly limited, because it is an item which should be individually decided according to specific symptoms, age, body weight and the like of the subject to be treated.

Preferably the normal dose range of 15 mg to 60 mg per adult patient (50-70 kg) on one administration based on a HA derivative can be exemplified, for more information the range of 0.3 mg to 1.2 mg per kg can be exemplified. And preferably the concentration of the injection solution can be exemplified from 0.5% to 3.0%, more preferably from 0.7% to 2.0% (as a cross-linking group-linked HA derivative) based on the total weight of the solution. The usage of the injection solution may preferably be exemplified single injection or two injections for one series of treatment. An injectable form of the pharmaceutical composition is the same.

One of the preferable embodiments of the injection solution and the injectable form of the pharmaceutical composition of the present invention can be exemplified below.

The properties of the cross-linked HA derivative are the following:

the weight average molecular weight of HA: 500,000 to 2,500,000, the compound of cross-linking group: cinnamic acid or cinnamic acid derivatives, the spacer compound: aminoalkyl alcohol, more preferably aminopentanol, aminobutanol, aminopropanol or aminoethanol, the DS of a cross-linking group: from 10% to 25%, and the degree of cross-linking: from 10% to 30%.

Medium: saline, phosphate buffered saline or water for injection

Concentration of the solution of cross-linked HA derivative: from 0.7% to 2.0%

Properties of the solution: having higher viscoelastic character and higher tread-formability than a solution of HA in the same concentration condition, and being capable of passing through a needle having from 18 to 25 gauge when extruded from the injection needle at 24° C. at a rate of 0.2 ml/second.

Moreover, the cross-linking extent can be preferably exemplified from 1.0% to 7.5%. And it has a moderate flowability, for example, the 1% by weight (as a cross-linking group-linked HA) of the cross-linked HA derivative gel is possible to form a continuous thread having a length of not less than 3 cm which is formed without break from a tip open end of an 23-guage injection needle when extruded from the injection needle at 24° C. at a rate of 0.2 ml/second in the direction of 45° downward from a horizontal direction.

In the present invention, a hydrogel state solution comprising cross-linked HA derivatives is mentioned in, for example, U.S. Pat. No. 6,602,859 the contents of which are incorporated herein by reference.

EXAMPLES

The present invention is described below more specifically based on Examples. However, there is no intention to limit the technical scope of the present invention by this.

Synthetic Example 400 mg of sodium hyaluronate having a weight-average molecular weight of 900,000 (manufactured by SEIKAGAKU CORPORATION) was mixed with a mixed solution containing water and dioxane under stirring. To the resultant solution was sequentially mixed 34 mg of N-hydroxy succinimide (HOSu)/1 ml of water (0.6 equivalent/HA disaccharide unit (mol/mol)); 29 mg of 1-ethyl-3-(3-dimethylamino-propyl)carbodiimide hydrochloride (EDCI.HCl)/1 ml of water (0.3 equivalent/HA disaccharide unit (mol/mol)); 51 mg of 4-(6-aminohexanamide)ethyl cinnamate hydrochloride/1 ml of water (0.3 equivalent/HA disaccharide unit (mol/mol)), at room temperature. The resultant mixture was stirred for 3 hours. The obtained mixture was further mixed with 200 mg of sodium hydrogen carbonate/3 ml of water, stirred for 2 hours, and then mixed with 400 mg of sodium chloride. Ethanol was charged into the resultant reaction solution to precipitate solid. The obtained solid was successively washed with 80% (vol./vol.) ethanol and ethanol, and then dried overnight at room temperature, thereby obtaining 360 mg of a white solid (4-(6-aminohexanamide)ethyl cinnamate-bound hyaluronic acid: "4-(6-aminohexanamide)ethyl cinnamate-bound hyaluronic acid" is hereinafter referred to merely int-HAD 1.

Further, the same procedure as above was conducted except that the equivalent amounts of N-hydroxy succinimide (HOSu), EDCI.HCl and cinnamate derivatives were changed as described hereinbelow, thereby obtaining int-HAD having different introduction percentages (degree of substitution) from each other.

(int-HAD 2) HOSu, EDCI.HCl and 3-aminopropyl cinnamate hydrochloride were respectively 0.2, 0.10 and 0.10 mol/mol HA disaccharide unit.

(int-HAD 3) HOSu, EDCI.HCl and 4-aminobutyl cinnamate hydrochloride were respectively 1.0, 0.5 and 0.5 mol/mol HA disaccharide unit.

(int-HAD 4) HOSu, EDCI.HCl and 5-aminopentyl cinnamate hydrochloride were respectively 1.4, 0.7 and 0.7 mol/mol HA disaccharide unit.

(int-HAD 5) HOSu, EDCI.HCl and 8-aminooctyl cinnamate hydrochloride were respectively 0.6, 0.3 and 0.3 mol/mol HA disaccharide unit.

(int-HAD 6) HOSu, EDCI.HCl and 3-aminopropyl cinnamate hydrochloride were respectively 0.2, 0.10 and 0.10 mol/mol HA disaccharide unit. The int-HAD 6 was prepared by the same method of int-HAD 2 preparation, except that the degree of 3-aminopropyl cinnamate was lower than that of int-HAD 2.

Then, the cinnamic acid derivative-introduced hyaluronic acids obtained from above (int-HADs 1-6) are respectively dissolved in a 5 mM phosphate-buffered physiological saline such that the concentration of the obtained solution became 1.0% by weight calculated as hyaluronic acid.

And the obtained solutions were respectively irradiated with ultraviolet rays for 20-40 minutes. These solutions were changed to gel form (hydrogel) by ultraviolet irradiation. The obtained gel is hereinafter referred to Crosslinked hyaluronate gel.

"Cross-linked hyaluronate gel" in the following experimental studies (herein occasionally referred to HA-Gel) was the gel which was irradiated with ultraviolet ray to 1.0% solution of int-HAD prepared by the above synthetic example. "1% sodium hyaluronate solution (1% HA-Na)" was used SUPARTZ®manufactured by SEIKAGAKU CORPORATION in the following experimental studies (hereinafter occasionally referred to HA-Na).

Both Cross-linked hyaluronate gel and 1% sodium hyaluronate solution (1% HA-Na) were used hyaluronic acid derived from chicken/rooster comb.

Example 1

Effects of Intra-Articular Injection of Cross-Linked Hyaluronate Gel (Ha-Gel) on the Anterior Cruciate Ligament (ACL) Transection Induced Arthritis in Rabbits Objective The rabbit ACL transection model used in this study has been accepted as an arthritis model, which produces cartilage degradation similar to OA in humans. Therefore, this model has been frequently used for evaluation of hyaluronan preparations (SUPARTZ®, HYALGAN®, HEALON®, SYNVISC®).

The objective of this study was to examine the efficacy of HA-Gel in the ACL transection model.

Methods

Experimental osteoarthritis (OA) was induced in 48 male rabbits by transecting the unilateral ACL. Four weeks after the ACL transection, HA-Gel was administered once or twice (at an interval of 2 weeks) into the joint cavity of the left hind knee at a dose of 0.05 mL/kg/joint. Its efficacy was compared to that of repeated administration of PBS or 1% sodium hyaluronate solution (1% HA-Na) once a week for 5 weeks. All animals were sacrificed 9 weeks after ACL transection. The left knee joints were then removed and evaluated by morphological assessment of cartilage degeneration, a volume of synovial fluid and protein content, a number of infiltrated cells and a glycosaminoglycans content in synovial fluid as indicators of synovitis, and safranin O stain of femoral condyles as histopathological examination of the cartilage and synovium.

The injection volume was set the same among all test substances.

Results

In morphological assessment, each animal was assessed for changes in two sites (femoral condyles and tibial plateaus) and total of 24 sites in each group were graded according to the following criteria:

Grade 1: Intact surface (No staining by Indian ink)
Grade 2: Minimal fibrillation (Surface retains the ink as elongated specks)
Grade 3: Overt fibrillation
Grade 4: Erosion (Loss of cartilage exposing the underlying bone)
    4a: 0 mm<Erosion≤2 mm in length
    4b: 2 mm<Erosion≤5 mm in length
    4c: 5 mm<Erosion in length
    4d: 5 mm×2 mm<Erosion (mm in length×width)

In the morphological assessment, cartilage degeneration was less in the HA-Gel groups compared to the 1% HA-Na (FIG. 1). In fact, in both the one- and two-injections HA-Gel groups, the degeneration of the articular cartilage was significantly less compared with control treated with 5-weekly injections of PBS. Moreover, considering the number of injections, the HA-Gel clearly showed to decrease the degeneration of the articular cartilage compared with 1% HA-Na. In contrast, 1% HA-Na administration decreased the cartilage degeneration compared with PBS, but the efficacy was not significant. The severity comparison among the test substances were in the following order: PBS>1% HA-Na>1 injection of HA-Gel≥2 injections of HA-Gel. Efficacy of HA-Gel for suppression of cartilage degeneration was also demonstrated by a reduction of the increase in chondroitin 6-sulfate (CS-6S) in the synovial fluid. In addition, HA-Gel appeared to improve the symptoms of synovitis, as judged from the reduction in increase of synovial fluid, protein and chondroitin 4-sulfate (CS-4S) contents.

In addition, that is reported that CS-6S in the synovial fluid is originated from cartilage and CS-4S in the synovial fluid is released through the blood vessels by inflammatory of synovial membrane. In other words, the reduction of the increase of CS-6S indicated to prevent the cartilage degeneration and the reduction of the increase of CS-4S indicated to prevent the inflammatory of synovial membrane.

Figure 2:
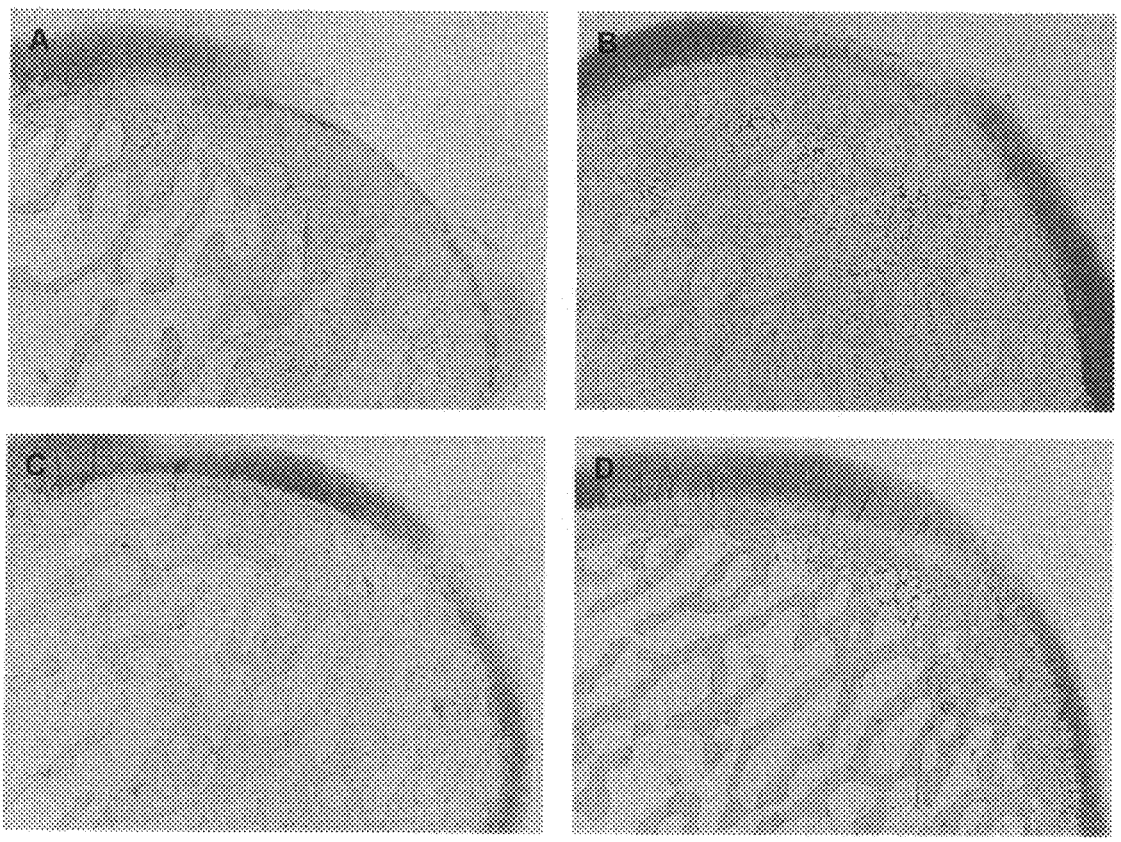
FIG. 2 is a histological finding (Safranin O/Fast green) of femoral condyles on ACL transection study in rabbits.

In FIG. 2, (A) is a typical specimen from the PBS group, (B) is a typical specimen from 1% HA-Na group, (C) is a typical specimen from 1 injection HA-Gel group, and (D) is a typical specimen from 2 injections HA-Gel group (original magnification×40).

The Safranin O stain displays glycosaminoglycans (GAGs) content within the cartilage (GAGs: red, Bone & collagen fibers: green).

The following observations were carried out and scored: area of cartilage matrix unstained/decreased staining for Safranin O, fissure formation in cartilage matrix, fibrillation of cartilage matrix, defect of cartilage, increase in number of chondrocytes, decrease in number of chondrocytes, remodeling of sub-cartilaginous bone and blood vessel invasion in cartilage matrix. The severity comparison among the test substances were in the following order: PBS>1% HA-Na>1 injection of HA-Gel>2 injections of HA-Gel.

Overall, since cartilage degeneration is milder when synovitis is not severe, these changes induced by HA-Gel may interact beneficially to relieve the progression of pathological changes. Histopathological findings of articular cartilage supported the macroscopic assessment (FIG. 2). In the histopathological examination of synovium, cuboidal/stratified synovial epithelium, subepithelial cellular infiltration, subepithelial fibrosis/edema, subepithelial hemorrhage and subepithelial calcium deposition were observed in all the experimental groups. These changes were less severe in HA-Gel groups compared to those in the PBS group.

Conclusion

These data show that in a rabbit ACL transection model of OA, the administration of HA-Gel once or twice (at an interval of 2 weeks) suppressed both synovitis and cartilage degeneration.

Example 2

Effects of Intra-Articular Injection of Cross-Linked Hyaluronate Gel (HA-Gel) on a Bradykinin-Induced Arthritic Pain in Rats Objective The arthritic pain model used in this study is a local pain model produced by injecting bradykinin (an endogenous hyperalgesic substance) with $PGE_2$ (a pain enhancer) into the joint cavity of rats. This model has been used to assess the analgesic effects of hyaluronan preparations based on the behavioral manifestations of joint pain in gait such as "lifting the foot", "claudication" and "walking on three legs". It has been reported that the analgesic effect assessed by this model was associated with the concentration of hyaluronan in synovial tissue.

The objective of this study was to examine the long-lasting analgesic effect of HA-Gel on arthritic pain induced by bradykinin in rats compared to 1% HA-Na and PBS.

Methods

The test substance was administered into the knee joint cavity of the left hind leg of female rats at a dose of 0.05 mL/joint. On weeks 1, 2 and 4 after administration, the mixture of bradykinin solutions and $PGE_2$ were injected into the same joint to induce arthritic pain. 1% HA-Na was only evaluated at 1 week, since this treatment typically requires reinjection once a week. Under blind conditions, the walking of the animal was observed for about 2 minutes after injection of bradykinin solutions and the severity of pain was scored on a 5-point scale (Table 1).

TABLE 1

Bradykinin-induced arthritic pain model:
Criteria for assigning pain scores

| Score | BEHAVIORAL MANIFESTATION |
|---|---|
| 0 | Normal or claudication for ≤5 sec |
| 1 | Claudication for 6-30 sec |

TABLE 1-continued

Bradykinin-induced arthritic pain model:
Criteria for assigning pain scores

| Score | BEHAVIORAL MANIFESTATION |
|---|---|
| 2 | Showing one of the following two manifestations:<br>Claudication for ≥31 sec<br>Lifting the foot for ≤5 sec |
| 3 | Showing one of the following two manifestations:<br>Lifting foot followed by claudication<br>Walking on three legs for ≤5 sec |
| 4 | Walking on three legs for ≥6 sec |

Results

Figure 3:
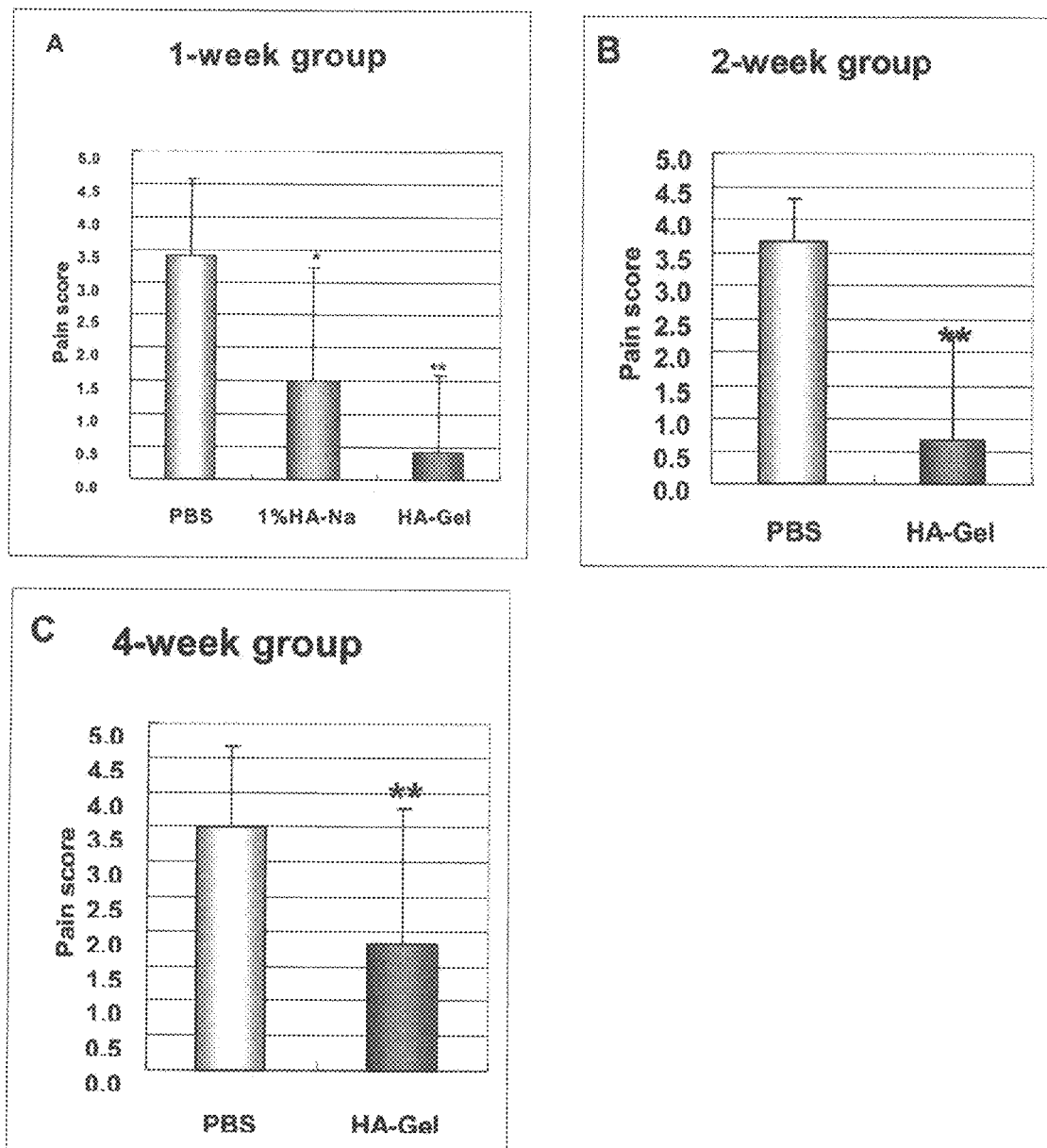
FIG. 3 is a graph showing analgesic effects of HA-Gel on bradykinin-induced arthritic pain model in rats. Pain score of PBS, Cross-linked hyaluronate gel (HA-Gel) or 1% HA-Na treated groups, wherein values are shown as mean±S.D. N=12 for each group; *$P<0.05$, **$P<0.01$ vs. PBS.

HA-Gel significantly suppressed the bradykinin-induced pain response compared with control group at the time points 1, 2 and 4 weeks post administration (FIG. 3). The analgesic effect by HA-Gel was more remarkable than that by 1% HA-Na at 1 week.

Conclusion

It was demonstrated that HA-Gel administered into the joint cavity was more effective against bradykinin-induced arthritic pain than PBS and 1% HA-Na tested as the positive control. As compared to controls, HA-Gel provided a sustained analgesic effect that lasted for at least 4 weeks.

Example 3

Effects of Intra-Articular Injection of Cross-Linked Hyaluronate Gel (HA-Gel) on the Silver Nitrate-Induced Arthritic Pain in Rats Objective The objective of this study was to examine the pain-relieving effect of HA-Gel on arthritic pain induced by silver nitrate in rats[3]. This model has been commonly used for the evaluation of the analgesic effect of numerous non-steroidal anti-inflammatory drugs (NSAIDs).

Methods

A 1% silver nitrate aqueous solution was injected into the knee joint cavity of the left hind leg of 42 male rats at a dose of 0.05 mL/joint. At 24 hours after injection, animals were allocated to groups according to the pain score while walking and the weight loading on the inflamed paw. The severity of pain was scored on the following 4-point scale; 0 point for normal or nearly normal, 1 score for mild claudication, 2 score for severe claudication and 3 score for walking on three legs. The weight loading was measured by using a weighting activity analgesia meter (manufactured by Tokken Inc.). HA-Gel, 1% HA-Na or PBS was administered at a dose of 0.05 mL/joint. On days 1, 2 and 3 after administration, the weight loading on the inflamed paw and pain score were assessed in the above same way. Items evaluated were the weight loading rate (%) (=loading on inflamed paw (g)/body weight (g)×100) and pain score while walking.

Results

Figure 4:
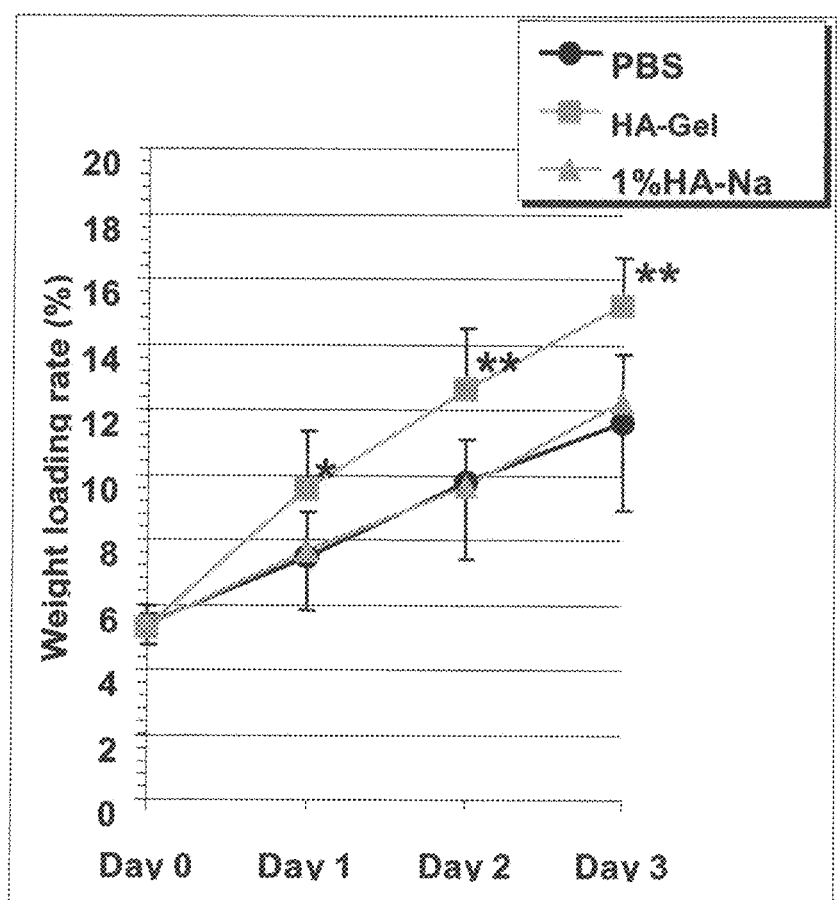
FIG. 4 is a graph showing silver nitrate-induced arthritic pain model: weight loading rate of PBS, HA-Gel or 1% HA-Na treated groups wherein values are shown as mean±S.D. N=10 for each group; *$P<0.05$**$P<0.01$ vs. PBS.
Figure 5:
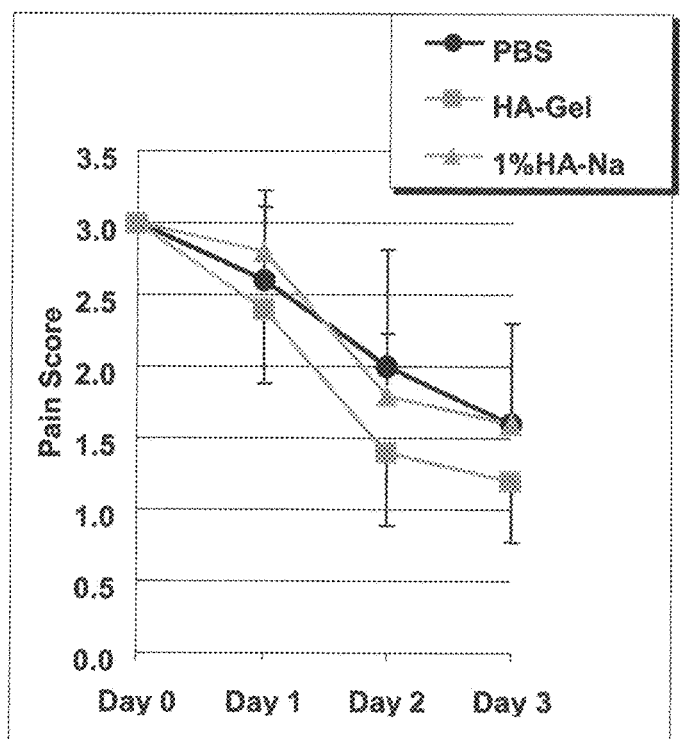
FIG. 5 is a graph showing silver nitrate-induced arthritic pain model: pain score of PBS, HA-Gel or 1% HA-Na treated groups wherein values are shown as mean±S.D. N=10 for each group.

At each time point on days 1 to 3 after administration of the test substance, the weight loading rate on the inflamed paw was significantly higher in animals given HA-Gel compared to those given PBS or 1% HA-Na (FIG. 4). In addition, the pain score of HA-Gel was lower than PBS or 1% HA-Na at each time point measured (FIG. 5).

Conclusion

These data demonstrate that HA-Gel administered into the joint cavity was more effective for inflammatory joint pain than PBS and 1% HA-Na.

Example 4

Analgesic Effect of Cross-Linked Hyaluronate Gel (HA-Gel) on Monosodium Urate-Induced Arthritic Joint Pain in Dogs Objective The deposit of micro-crystals of monosodium urate (MSU) in synovial fluid promotes acute inflammatory joint pain in humans. The experimental joint pain model induced by an intra-articular injection of MSU crystals has been widely used to evaluate the analgesic efficacy of sodium hyaluronate and non-steroidal anti-inflammatory drugs.

The objective of this study was to examine the analgesic effect of HA-Gel on joint pain induced by MSU in dogs.

Methods

HA-Gel, physiological saline or 1% HA-Na was administered to female beagle dogs by an intra-articular injection into the knee joint cavity of the left hind limb at a dose of 0.3 mL/kg/joint. Monosodium urate (MSU), a substance which induces inflammation and severe pain, was then injected at the same joint 0.5 or 72 hours after the test material treatment. At 2, 3, 4, 5, 6 and 8 hours after the injection of MSU, gait condition was scored and weight-bearing rates of the left hind limb were calculated as the joint pain indicators. The area under the time curve (AUC) was calculated from both these indicators.

Gait was observed and the condition of the gait was scored (indicated as abnormal gait score) according to the following criteria; 0: Unchanged (Normal gait), 1: Mild (Stands normally but gait is unnatural), 2: Moderate (Stands on 4 limbs but often raises left hind limb (injection site)), 3: Severe (Touches only the tip of the left hind limb to the ground when walking) and 4: Very severe (Cannot put any weight on left hind limb; walking on 3 limbs). In addition, three scales were used for the weight-bearing measurement: scale A was a digital platform scale (DP-6100GP; Yamato Scale Co., Ltd); and scales B and C were load-cell digital platform scales (DP-6000; Yamato Scale Co., Ltd.). The front limbs were placed on scale A, the right hind limb on scale B, and the left hind limb on scale C. The values from all three scales were recorded to the nearest 0.1 kg. The weight-bearing rate was calculated by using the following formula.

$$\text{Weight-bearing rate}=100\times\text{Mean}C/(\text{Mean}A+\text{Mean}B+\text{Mean}C)$$

Results

Figure 6:
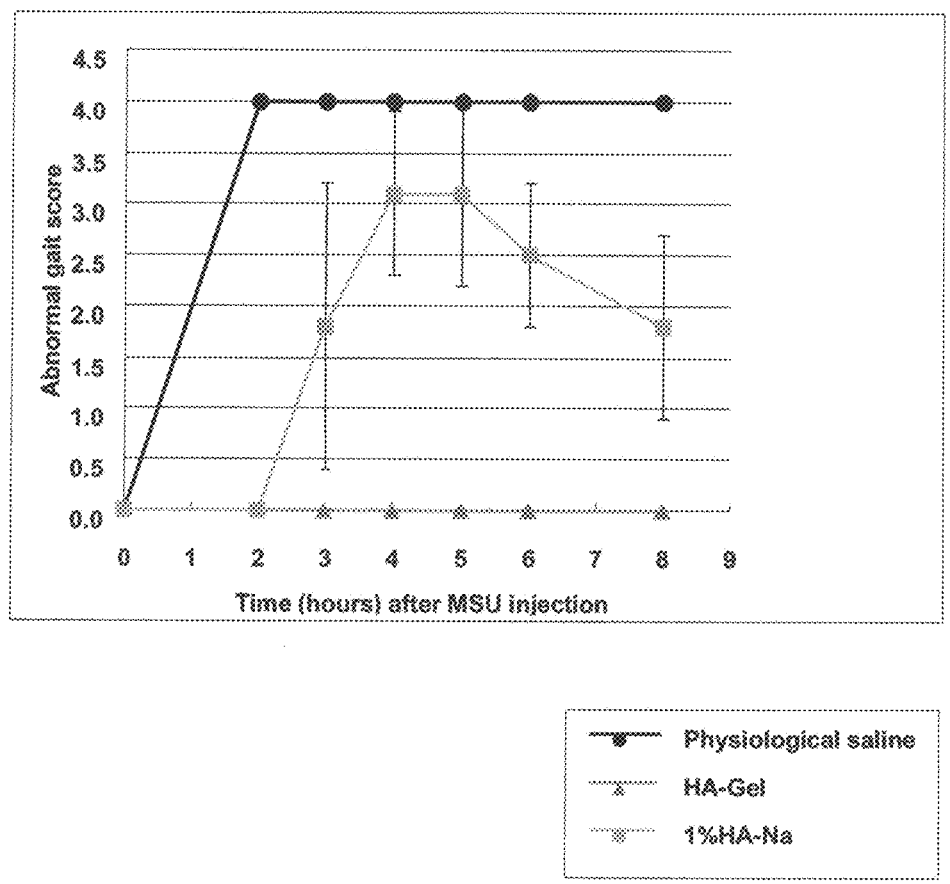
FIG. 6 is a graph showing monosodium urate-induced arthritic joint pain model: changes in abnormal gait score. Physiological saline, Cross-linked hyaluronate gel (HA-Gel) and 1% HA-Na were administered intra-articularly 0.5 hour before MSU injection. Values are shown as mean±S.D. N=12 for each group.

In experiments where MSU was injected 0.5 hour after the test material treatment, the mean AUCs of abnormal gait score were 0.0, 28.0 and 13.5 in HA-Gel, physiological saline and 1% HA-Na, respectively (FIG. 6, Table 2). HA-Gel exhibited a complete analgesic effect and no painful walking was observed in all of the treated animals. 1% HA-Na also exhibited a significant analgesic effect, as compared to physiological saline, but the effect was significantly lower than that of HA-Gel.

Figure 7:
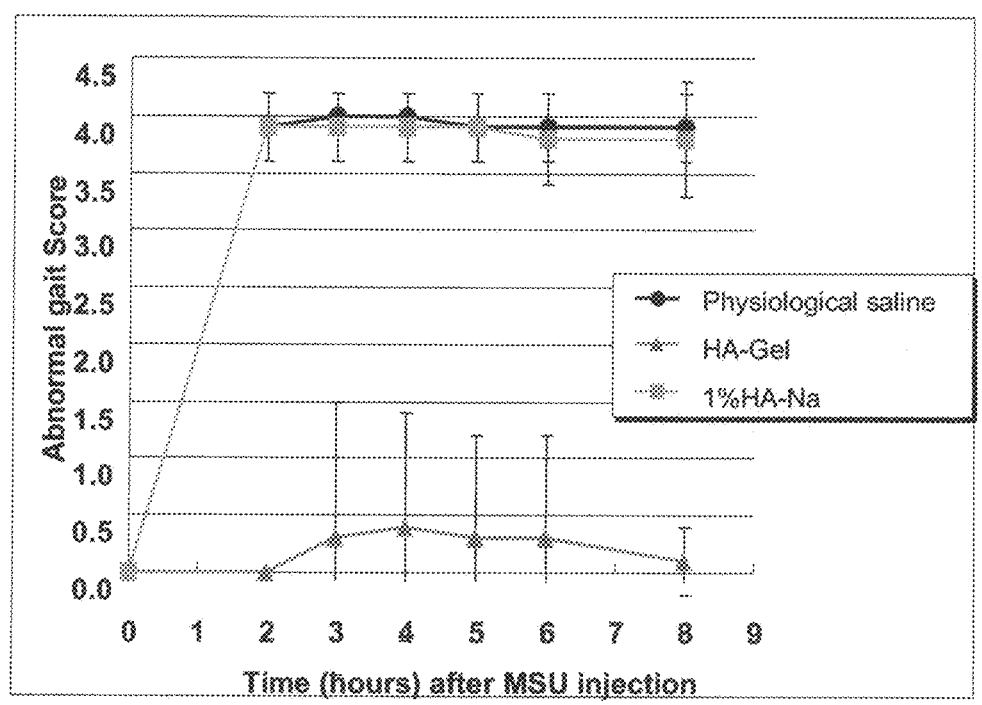
FIG. 7 is a graph showing monosodium urate-induced arthritic joint pain model: changes in abnormal gait score. Physiological saline, Cross-linked hyaluronate gel (HA-Gel) and 1% HA-Na were administered intra-articularly 72 hours before MSU injection. Values are shown as mean±S.D. N=12 for each group.

In experiments where MSU was injected 72 hours after the test material treatment, the AUCs of abnormal gait score were 1.5, 27.6 and 27.1 in HA-Gel, physiological saline and 1% HA-Na, respectively (FIG. 7, Table 3). HA-Gel still exhibited a significant analgesic effect, whereas the effect of 1% HA-Na on the knee joint pain was almost completely diminished.

In both the experiments, changes in the weight-bearing rates of the left hind limb were consistent with those of the abnormal gait scores.

TABLE 2

Monosodium urate-induced arthritic joint pain model: AUC of abnormal gait score.

| Group | Number of animals | AUC of abnormal gait score |
|---|---|---|
| Physiological saline (0.3 mL/kg) | 12 | 28.0 ± 0.0 |
| Cross-linked hyaluronate gel (HA-Gel) (0.3 mL/kg) | 12 | 0.0** ± 0.0 |
| 1% HA-Na (0.3 mL/kg) | 12 | 13.5**,## ± 3.2 |

Physiological saline, HA-Gel and 1% HA-Na were administered intra-articularly 0.5 hours before MSU injection.
**$p < 0.01$: Significant difference from Physiological saline (Tukey-Kramer multiple comparison test)
$p < 0.01$: Significant difference from Cross-linked hyaluronate gel (Tukey-Kramer multiple comparison test)

TABLE 3

Monosodium urate-induced arthritic joint pain model: AUC of abnormal gait score.

| Group | Number of animals | AUC of abnormal gait score |
|---|---|---|
| Physiological saline (0.3 mL/kg) | 12 | 27.6 ± 1.1 |
| Cross-linked hyaluronate gel (HA-Gel) (0.3 mL/kg) | 12 | 1.5** ± 4.5 |
| 1% HA-Na (0.3 mL/kg) | 12 | 27.1## ± 2.1 |

Physiological saline, HA-Gel and 1% HA-Na were administered intra-articularly 72 hours before MSU injection.
**$p < 0.01$: Significant difference from Physiological saline (Tukey-Kramer multiple comparison test)
$p < 0.01$: Significant difference from Cross-linked hyaluronate gel (Tukey-Kramer multiple comparison test)

Conclusion

It was confirmed that the single intra-articular administration of HA-Gel suppressed the MSU-induced arthritic knee joint pain. Compared to 1% HA-Na, the analgesic effect of HA-Gel was superior and more prolonged.

Example 5

Residual Ratio of Cross-Linked Hyaluronate Gel (HA-Gel) in Joint Cavity and Synovium of the Knee in Rabbits Objective The objective of the study was to investigate the local retention of intra-articularly injected HA-Gel in rabbits.

Methods

HA-Gel and its non-cross-linked intermediate (int-HAD) were administered into the both right and left knee joint cavity in male rabbits at a dose of 0.05 mL/kg/joint (the concentrations of HA-Gel and int-HAD: 1%). Animals were sacrificed on days 1, 3, 5, 7, 14 and 28 after administration, and synovial fluid and synovium were collected. A remaining cross-linking agent of Cross-linked hyaluronate gel, trans-cinnamic acid (tCA), was quantified by high performance liquid chromatography (HPLC) to calculate the residual ratios of HA-Gel and int-HAD.

Results

Residual percentage was calculated from the measured value by HPLC.

About the metabolic disposition of the hyaluronate with extraneous administration to the joint cavity it is known commonly that the hyaluronate migrates gradually from the synovial fluid to the synovium.

Figure 8:
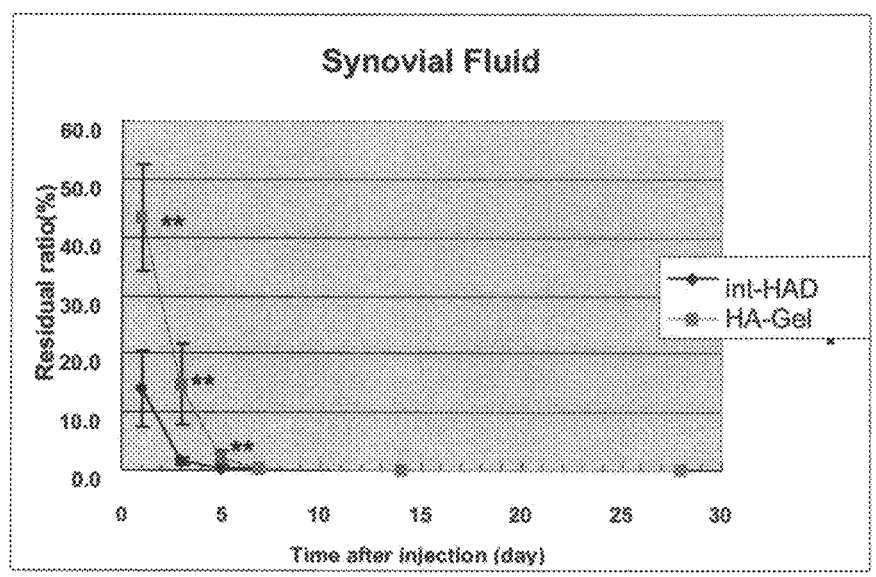
FIG. 8 is a graph showing residual ratio of HA-Gel in synovial fluid of the knees. Values are shown as mean±S.D. N=5 (10 joints) for each group at each time point; **$P<0.01$ vs. int-HAD.
Figure 9:
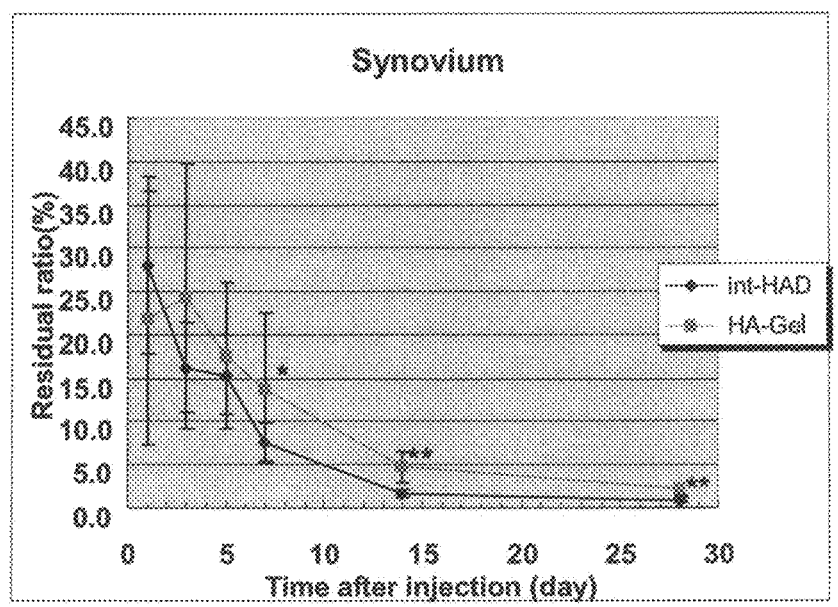
FIG. 9 is a graph showing residual ratio of HA-Gel in synovium of the knees. Values are shown as mean±S.D. N=5 (10 joints) for each group at each time point; *$P<0.05$, **$P<0.01$ vs. int-HAD.

Most of the HA-Gel disappeared from the synovial fluid within 7 days, however, it remained in the synovium for up to 28 days after administration. By comparing the residual ratios of HA-Gel and int-HAD, significantly higher levels of HA-Gel were detected in the synovial fluid on days 1, 3, and 5 after administration (FIG. 8). According to FIG. 8, the HA-Gel remained in the synovial fluid to about 15% of the administered HA-Gel on 3 days after administration. However, in the synovium, the ratios of Cross-linked hyaluronate gel remained significantly higher on days 7, 14, and 28 (FIG. 9).

Conclusion

Compared to non-cross-linked hyaluronan, the injected HA-Gel remained in synovial fluid and synovium for a prolonged period of time. On the other hand, non-cross-linked hyaluronan diffused out of the synovial fluid rapidly, with lower levels retained in the synovium. So, HA-Gel can remain in long-term existence in the joint (i.e., at administration site), because it migrates more slowly from the synovial fluid to the synovium and is more gradually metabolized in comparison with int-HA. The increased retention of HA-Gel may contribute to a superior cartilage protective effect and a long-lasting analgesic effect.

Example 6

Effects of Intra-Articular Injection of Cross-Linked Hyaluronate Gel (HA-Gel) on the Papain-Induced Arthritis in Rabbits The rabbit papain induced arthritis model used in this study has been accepted an osteoarthritis (OA) model produced by injecting papain (a cysteine protease present in papaya) into the knee joint cavity of rabbits.

The objective of this study was to examine the efficacy of HA-Gel in the papain-induced arthritis model. This study was performed twice.

Rabbits (21-week-old male) were fixed in a supine position under ketamine general anesthesia (1 mL/head, i.v.), and a wide area around the knee joint of the left hind leg was shaved with an electric clipper. The injection site of the knee joint was sterilized with 70% ethanol and Isodine® solution.

After that, 0.8% papain solution was administered twice (at an interval of 3 days) into the joint cavity of the left hind knee at a dose of 500 µL/joint.

Total 20 rabbits, 5 rabbits for each group, were used in this study. The papain solution was activated by L-Cysteine immediately prior to the injection.

One week after the second injection of papain, 150 µL of the test substance (HA-Gel or phosphate buffered saline (PBS)) was administered into the knee joint cavity of the left hind leg once per week for 3 weeks.

All animals were sacrificed 1 week after the last administration of the test substances. The left knee joints were then removed and synovial fluid and synovium were collected from the left knee joint.

The left knee joints were evaluated by morphological examination, histopathological examination of the synovium and articular cartilage, volume of synovial fluid and protein content. As histopathological examinations, paraffin sections were made from formalin-fixed synovium and stained with hematoxylin-eosin (HE) and alucian-blue. After the EDTA decalcification and safranin O staining, the cartilage conditions were observed in the femoral condyles and tibial plateaus.

Figure 10:
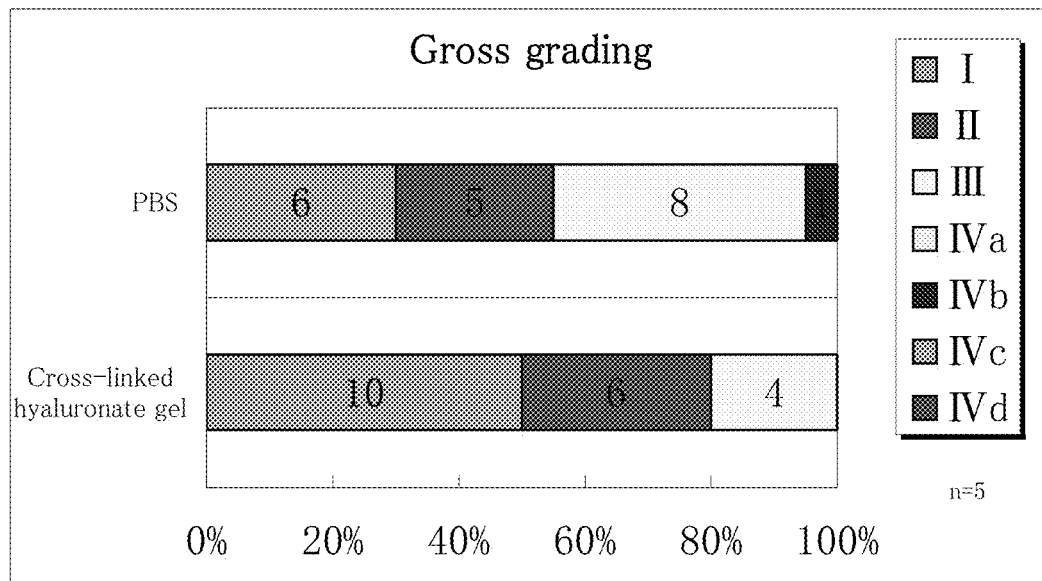
FIGS. 10 and 11 are graphs showing papain-induced arthritis model: gross morphological assessment of cross-linked hyaluronate gels and PBS.
Figure 11:
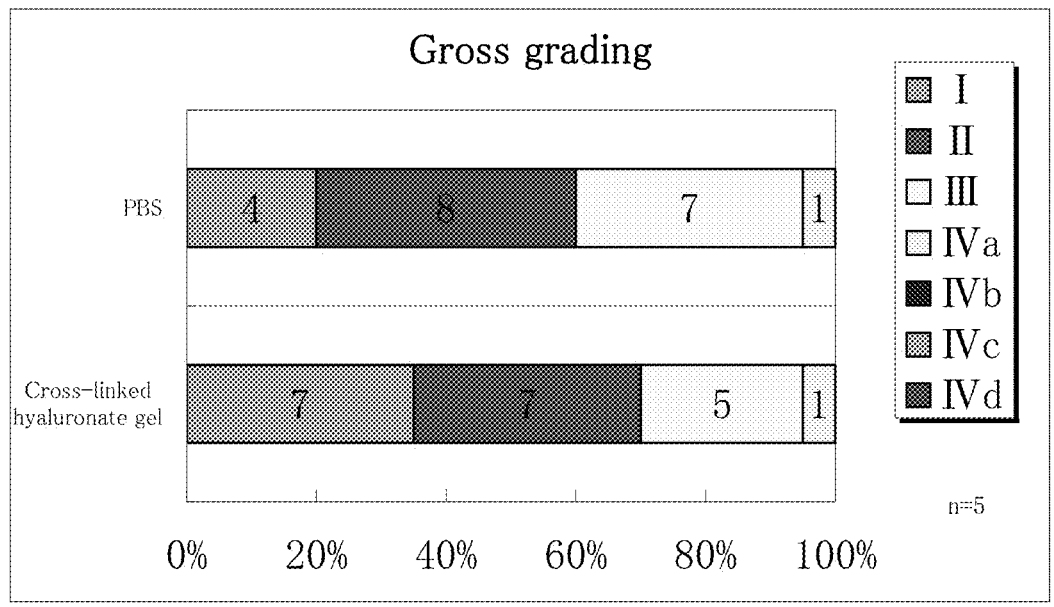

In the morphological assessment, degeneration severity was scored on the same criteria of Example 1 (FIGS. 10 and 11). Cross-linked hyaluronate gels alleviated the cartilage degeneration compared to PBS. However, the efficacy was not significant. It is considered that the number of animals is not enough.

In the histopathological examination of cartilage, the degeneration of cartilage matrix, chondrocyte decrement and decreased staining for safranin O were alleviated by HA-Gel.

HA-Gel used in this study suppressed the cartilage degeneration compared to PBS.

Cross-linking extents of cross-linked hyaluronate gels used in this study were respectively 1.72% (FIG. 10) and 2.06% (FIG. 11) and was lower than HA-Gel used in other example studies. It is considered that the degree of the cross-linking extent is essential to achieve significant efficacy on improvement of the arthritic pain and the cartilage degeneration.

INDUSTRIAL APPLICABILITY

According to these above examples, it was demonstrated that the intra-articular injection of HA-Gel once or twice (at an interval of 2 weeks) had the same or much higher effectiveness than five injections of HA-Na for treatment of knee OA. And also it is confirmed that HA-Gel also provided a therapeutic efficacy in animal models for evaluation of NSAIDs.

When HA-Gel was injected into the knee joint cavity, most of the HA-Gel disappeared from the synovial fluid within 7 days. However, it remained in the synovium for up to 28 days after administration. Since it is considered that the concentration of hyaluronan in synoviun correlated with the analgesic effect, the increased retention of HA-Gel may contribute to a long-lasting analgesic effect. Moreover, HA-Gel is expected to be well shock absorber to relieve pain and improve knee function in OA, since it has a higher viscoelasticity than HA-Na solution.

It may be proposed a therapeutic agent for joint diseases which has the following merits; a long-lasting effect by single injection, a decrease of number of doses for one series of treatment, and a reduction of the risk of infection in an intra-articular administration. Consequently stresses on affected patients of joint disorders can be lowered.

The invention claimed is:

1. A method for treating an arthritic disorder which comprises injecting, into an intra-articular area or a joint, a pharmaceutical composition in the form of an injectable solution of a cross-linked hyaluronate gel wherein a 1% solution of the hyaluronate capable of being extruded from a 23-gauge injection needle at 24° C. under a pressure of 5.0 Kg/cm$^2$, comprising:
    (a) a cross-linked hyaluronic acid derivative wherein part of functional groups of hyaluronic acid are cross-linked to each other with a cross-linking group, said cross-linked hyaluronic acid derivative having following characteristics:
        (i) a cross-linking extent of functional groups of the hyaluronic acid is 1% to 7.5% based on a total number of constituent disaccharide units of the hyaluronic acid,
        (ii) the cross-linking group is a residue of cinnamic acid or a cinnamic acid derivative,
        (iii) a degree of substitution of a cross-linking group is from 10% to 25%, and
        (iv) a degree of cross-linking in the cross-linked hyaluronic acid derivative is from 10% to 30%, and
    (b) a pharmaceutically acceptable aqueous medium.

2. The method according to claim 1, wherein the cross-linked hyaluronic acid derivative has a spacer between the cross-linking group and the functional groups of the hyaluronic acid, and wherein the spacer is a residue of aminoalkyl alcohol.

3. The method according to claim 1, wherein the cross-linked hyaluronic acid derivative in the pharmaceutical-composition has a concentration of 0.5% to 3.0% by weight based on the total weight of the solution composition.

4. The method according to claim 2, wherein the cross-linked hyaluronic acid derivative in the pharmaceutical composition has a concentration of 0.5% to 3.0% by weight based on the total weight of the solution composition.

5. The method according to claim 1, wherein the cross-linked hyaluronic acid derivative in the pharmaceutical composition has a concentration of 1% by weight based on the total weight of the composition.

6. The method according to claim 2, wherein the cross-linked hyaluronic acid derivative in the pharmaceutical composition has a concentration of 1% by weight based on the total weight of the composition.

7. The method according to claim 1, wherein the treating an arthritic disorder comprises alleviating joint pain associated with the arthritic disorder.

8. The method according to claim 2, wherein the treating an arthritic disorder comprises alleviating joint pain associated with the arthritic disorder.

9. The method according to claim 3, wherein the treating an arthritic disorder comprises alleviating joint pain associated with the arthritic disorder.

10. The method according to claim 5, wherein the treating an arthritic disorder comprises alleviating joint pain associated with the arthritic disorder.

11. The method according to claim 6, wherein the treating an arthritic disorder comprises alleviating joint pain associated with the arthritic disorder.

12. The method according to claim 7, wherein an analgesic effect lasts for two weeks or more after the injecting.

13. The method according to claim 9, wherein an analgesic effect lasts for two weeks or more after the injecting.

14. The method according to claim 10, wherein an analgesic effect lasts for two weeks or more after the injecting.

15. The method according to claim 11, wherein an analgesic effect lasts for two weeks or more after the injecting.

16. The method according to claim 1, wherein the cross-linked hyaluronic acid derivative is administered in a unit dosage of 0.3 mg to 1.2 mg per kg of an adult patient.

17. The method according to claim 1, wherein the aqueous medium comprises at least one of water for injection, physiological saline, and phosphate buffered saline.

18. The method according to claim 1, wherein the aqueous medium is phosphate buffered saline.

19. A method for alleviating joint pain associated with treating an arthritic disorder in a knee which comprises injecting into the knee a pharmaceutical composition in the form of an injectable solution of a cross-linked hyaluronate gel wherein a 1% solution of the hyaluronate capable of being extruded from a 23-gauge injection needle at 24° C. under a pressure of 5.0 Kg/cm$^2$ and having an analgesic effect that lasts for two weeks or more after the administering comprising:
    (a) a cross-linked hyaluronic acid derivative wherein part of functional groups of hyaluronic acid are cross-linked to each other with a cross-linking group, said cross-linked hyaluronic acid derivative having following characteristics:

(i) a cross-linking extent of functional groups of the hyaluronic acid is 1% to 7.5% based on a total number of constituent disaccharide units of the hyaluronic acid,
(ii) the cross-linking group is a residue of cinnamic acid or a cinnamic acid derivative,
(iii) a degree of substitution of a cross-linking group is from 10% to 25%, and
iv) a degree of cross-linking in the cross-linked hyaluronic acid derivative is from 10% to 30%, and
(b) a pharmaceutically acceptable aqueous medium.

20. The method according to claim 19, wherein the cross-linked hyaluronic acid derivative in the pharmaceutical composition has a concentration of 0.5% to 3.0% by weight based on the total weight of the composition.

21. The method according to claim 20, wherein the cross-linked hyaluronic acid derivative in the pharmaceutical composition has a concentration of 1% by weight based on the total weight of the composition.

* * * * *

UNITED STATES PATENT AND TRADEMARK OFFICE
CERTIFICATE OF CORRECTION

PATENT NO.      : 8,889,652 B2                                    Page 1 of 1
APPLICATION NO. : 12/448064
DATED           : November 18, 2014
INVENTOR(S)     : K. Miyamoto et al.

It is certified that error appears in the above-identified patent and that said Letters Patent is hereby corrected as shown below:

In The Claims
Column 19, line 47 (Claim 1, line 5) of the printed patent, "hyaluronate capable" should be -- hyaluronate gel is capable --.
Column 19, line 48 (Claim 1, line 6) of the printed patent, "24° C." should be -- 24 °C. --.
Column 20, line 7 (Claim 3, line 4) "the solution composition" should be -- the composition --.
Column 20, line 11 (Claim 4, line 4) "the solution composition" should be -- the composition --.
Column 20, line 57 (Claim 19, line 5) of the printed patent, "hyaluronate capable" should be -- hyaluronate gel is capable --.
Column 20, line 58 (Claim 19, line 5) of the printed patent, "24° C." should be -- 24 °C. --.

Signed and Sealed this
Twelfth Day of July, 2016

Michelle K. Lee
*Director of the United States Patent and Trademark Office*